United States Patent [19]

Olerud

[11] Patent Number: 5,267,999

[45] Date of Patent: Dec. 7, 1993

[54] CLAMP FOR USE IN SPINAL SURGERY

[76] Inventor: Sven Olerud, Box 4, Lännaholm, Sweden

[21] Appl. No.: 883,580

[22] Filed: May 15, 1992

[30] Foreign Application Priority Data

May 15, 1991 [SE] Sweden .................. 9101462

[51] Int. Cl.⁵ .................. A61B 17/56; A61F 2/28
[52] U.S. Cl. .................. 606/61; 623/16
[58] Field of Search .......... 606/57, 59, 60, 61, 606/67, 69, 70, 64, 65, 104, 72, 73; 623/16; 128/69

[56] References Cited

U.S. PATENT DOCUMENTS

| | | | |
|---|---|---|---|
| 4,361,141 | 11/1982 | Tanner | 606/61 |
| 4,369,769 | 1/1983 | Edwards | 606/61 |
| 4,448,191 | 5/1984 | Rodnyansky | 606/61 |
| 4,611,582 | 9/1986 | Duff | 606/61 |
| 4,641,636 | 2/1987 | Cotrel | 606/61 |
| 4,827,918 | 5/1989 | Olerud | 606/61 |
| 5,000,165 | 3/1991 | Watanabe | 606/61 |
| 5,057,109 | 10/1991 | Olerud | 606/61 |
| 5,074,864 | 12/1991 | Cozad | 606/61 |
| 5,116,334 | 5/1992 | Cozad | 606/61 |

FOREIGN PATENT DOCUMENTS

| | | | |
|---|---|---|---|
| 2642642 | 8/1990 | France | 606/61 |
| 356987 | 8/1969 | Sweden . | |
| 9119469 | 12/1991 | World Int. Prop. O. | 606/61 |

Primary Examiner—Michael A. Brown
Attorney, Agent, or Firm—Finnegan, Henderson, Farabow, Garrett & Dunner

[57] ABSTRACT

A surgical clamp which can be affixed to a vertebra without requiring the use of fastener elements which are driven or screwed into the vertebra includes a first block (1) from which there extend two projections or blades (3, 4) to form a fork structure which can straddle the vertebra arch in the region between the spinal processus and the processus articularis, and further includes a tensioning element (7) in the form of a rod which extends through the first block (1) and one end of which is curved to form a hook (10) for gripping around a lamina and the other end of which is screw threaded and coacts with nut (11) which is guided in the block and one end of which has a tool accommodating recess.

18 Claims, 1 Drawing Sheet

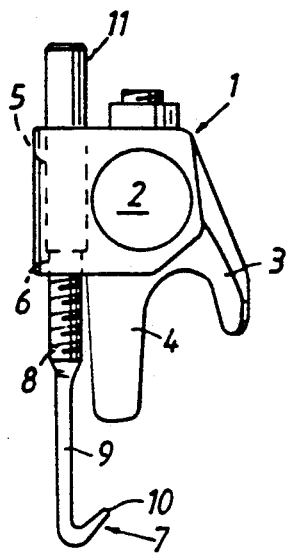
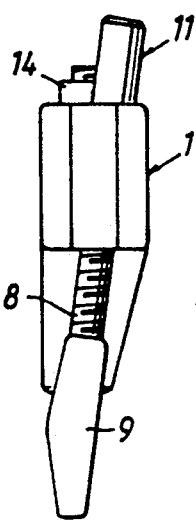
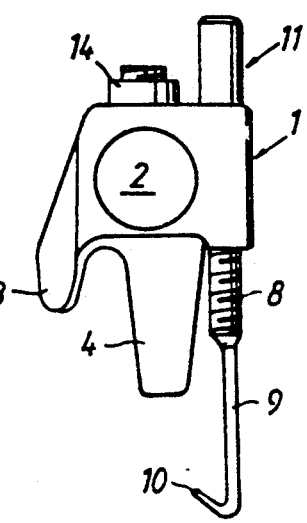
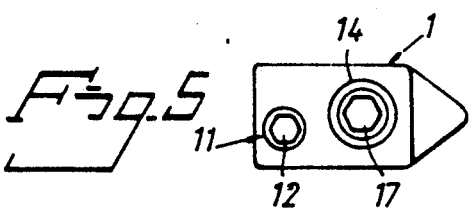
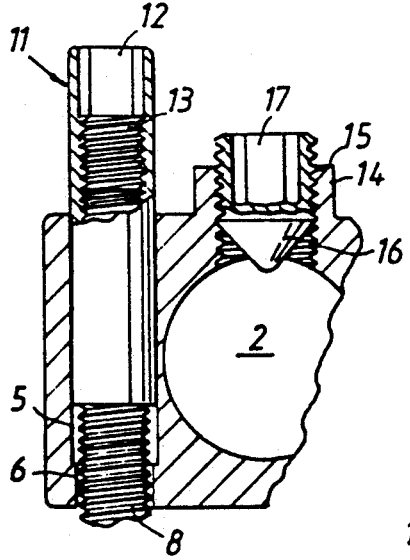
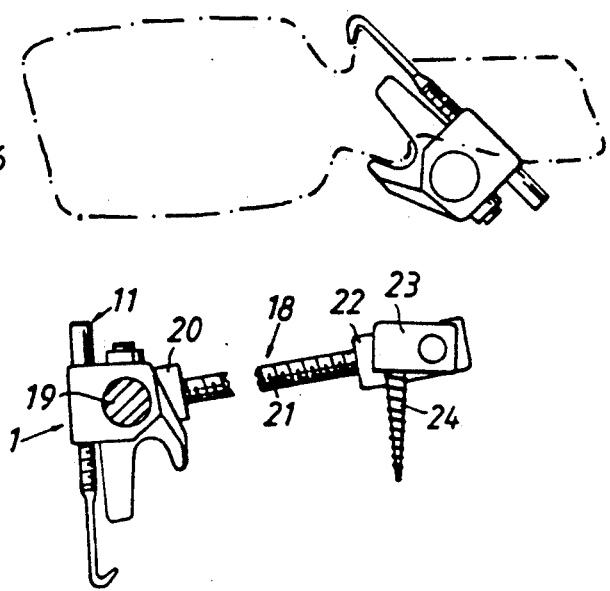

1

CLAMP FOR USE IN SPINAL SURGERY

FIELD OF INVENTION

The present invention relates to a clamp for use in spinal surgery, which can be attached firmly to a vertebra without the use of bone screws or like devices which must be driven or screwed into the bone or bone substance of the vertebra.

BACKGROUND ART

Present day commercially available vertebrae clamps are encumbered with shortcomings and a number of serious drawbacks. The known clamps are not always fixated effectively at the vertebra concerned in a manner which will enable the vertebra to be set to an optimally corrected position in a controlled fashion. Another shortcoming of known clamps of this kind is that it is necessary to construct the clamp in a manner which will avoid damaging the bone surface of the vertebra or its bone substance, so that the bone will not be weakened and the clamping force retained. The primary object of the invention is to provide a vertebra clamp which can be clamped swiftly and simply to a vertebra, in a fully stable fashion, without causing damage to the bone substance of the vertebra held by the clamp. A further object of the invention is to provide a clamp which can be oriented automatically on the vertebra in a manner which will enable the clamp to be included in the spine fixating instruments described in U.S. Pat. Nos. 4,827,918 and 5,057,109.

These and other objects of the invention are achieved with the inventive surgical clamp defined in the following claims.

So that the invention will be more readily understood and other features thereof made more apparent, the invention will now be described in more detail with reference to an exemplifying embodiment thereof and also with reference to the accompanying drawing, in which:

BRIEF DESCRIPTION OF THE DRAWINGS

FIG. 1 is a schematic side view of the inventive clamp;

FIG. 2 is a schematic illustration showing the clamp from one end, (the dorsal aspect);

FIG. 3 is a schematic illustration showing the clamp from the side opposite to that shown in FIG. 1, (the medial aspect);

FIG. 4 is a schematic illustration similar to the illustration shown in FIG. 2 but from the other end, (the ventral end);

FIG. 5 is a schematic illustration showing the clamp from the top and from the manipulating side thereof;

FIG. 6 is a schematic illustration showing in larger scale part of the clamp shown in FIG. 1; and FIG. 7 is a schematic illustration showing the inventive clamp in use with a fixating element and attached to a vertebra.

BEST MODE OF CARRYING OUT THE INVENTION

The novel clamp includes a generally rectangular first block, which is referenced generally 1 and which in the illustrated case is provide with a penetrating hole 2 for a reason hereinafter explained.

Extending from the ventral side of the first block 1 is a relatively short first projection, which is referred to hereinafter as the first blade 3. As will be seen from the drawing, the first blade has surfaces which are inclined at different angles and in different directions so as to adapt the blade to the anatomical configuration of the vertebra with which the clamp is used. In other respects, the blade has a gently rounded configuration.

Also extending from the ventral part of the clamp is a second projection or second blade 4 which is remote from the first blade 3 and which together with said blade 3 forms a fork-like structure which is intended to be placed beneath an appropriate part of the vertebra concerned. This will enable the block to straddle the caudal part of the vertebra arch.

The second blade 4 is generally flat and planar and also comparatively thin.

A first bore 5 extends from the caudal part of the block 1 in a plane essentially parallel to the second blade 4 and in the close proximity of said blade (FIG. 1), said first bore merging with a second bore 6 of smaller diameter than said first bore so as to define an annular shoulder, and, of course, coaxial therewith.

As will best be seen from FIG. 2, both of the bores 5 and 6 are inclined, when seen from the ends of the clamp. The bores function to accommodate the other main part of the clamp, this other clamp part comprising a tensioning element, generally referenced 7, comprised of screw threaded rod 8 which merges with a flat part 9 of generally rectangular cross-section. The flat part 9 is curved at its free end to form a hook 10, which also has a rectangular cross-section.

The tensioning element is intended for coaction with an externally cylindrical nut 11 which, as shown in FIG. 6, has internal spanner engaging surfaces 12 for coaction with an appropriate spanner, key or like tool, and which has an internal screw thread 13 for coaction with the threaded part 8 of the tensioning element 7 so as that the element 7 will move axially in response to rotation of the nut 11.

The clamp also includes a screw 16 which has a conical end surface, while provided at the top of the screw is a spanner engaging hexagon of the same size as the hexagon 12.

When the surgeon wishes to anchor the described clamp to a vertebra, he first ensures that the major part of the tensioning element 7 is unscrewed or backed off from the nut 11 and then places an appropriate tool in the hexagonal recess 12, so as to grip the clamp firmly, and positions the clamp so that the blades 3 and 4 straddle the vertebra arch, within the region between the spinal processus and the processus articularis.

Because the tensioning element 7 is located in the close proximity of the second blade 4, as before mentioned, it will retain its direction of orientation when the nut is tightened, so that at the beginning of the tightening sequence, the hooked part 10 of the tensioning element will be in a position to grip automatically around a lamina.

The surgeon need therefore only continue to tighten the nut 11 in order to achieve the desired fixation, in which the hook 10 of the tensioning element 7 grips around the lamina and the hook formed on the first block 1 by the first and second blades 3,4 grips around the vertebral arch between the spinal processus and the processus articularis.

Thus, the clamp can be fitted to a vertebra quickly and with a simple hand manipulation, and the vice-like anchorage obtained provides a very stable connection between vertebra and clamp.

As before mentioned, the second blade 4 is thin and is initially loosely applied.

The aforedescribed clamp is intended primarily for inclusion in a fixation instrument of the kind taught by U.S. Pat. No. 4,827,918, wherein one part of the instrument is intended to be connected to the sacrum in a conventional manner with the aid of bone screws, whereas the other part is intended to be attached to a vertebra without the use of pedicular screws or other securing devices which grip into the vertebra. The inventive clamp therefore forms a part of the fixation instrument, as shown in FIG. 7.

In addition to the inventive clamp, the fixation instrument, referenced generally 18 in the drawing, includes a shaft 19 which fits into the aforesaid hole 2 provided in the first block 1. Although not shown, the first block 1 is provided with a further hole into which a second block 20 is fitted, said shaft also coacting with the second block in a manner to journal the first and second blocks one to the other. As will be seen from FIG. 7, the second block is steered by a spindle or screw 21 which extends thereinto and which at its other end is so connected to a third block 22, in a known manner, such that the second and third blocks will move towards and away from one another in response to rotation of the spindle about its long axis. The third block 22 is rotatably connected to a fourth block 23, which is connected to the sacrum with the aid of one or more bone screws 24.

It should be particularly noted that the clamp, which is initially applied loosely to the lamina of the vertebra, will have adapted its position and orientation in relation to the remaining parts of the fixation instrument through the medium of the shaft 19 prior to completion of the tightening sequence, since the instrument has been position in conjunction with fixing the same to the sacrum. Subsequent to having fixed the instrument to the sacrum, fixation to the vertebra is made definite by tightening the nut 11 on the tensioning element 7.

As before mentioned, a wrongly positioned vertebra connected to the inventive clamp can be moved to optimum position of correction with the aid of a mechanical repositioning system connected to the clamp and to the sacrum block respectively. In this case, the connection between the clamp and the second block 20 and the connection between the fourth block 23 and the third block 22 are moveable, so that when a correct position is reached, the connections can be locked positively and securely with the aid of stop screws, referenced 17 on the clamp.

It should be noted that the rod 8-10 and/or the nut 11 are so constructed and fitted in the first block 1 as to generate between the rod/nut and said block a frictional force which is sufficient to maintain a given setting.

I claim:

1. A surgical clamp comprising:
   a rectangular first block defining a leadway;
   first and second projections extending from said first block, said first and second projections having parallel longitudinal axes and being mutually spaced so as to form a fork for straddling a first part of a skeleton, the fork defining surfaces adapted to cooperate with said first part of the skeleton; and
   a tension rod positioned in said leadway and being substantially parallel to the longitudinal axes of said first and second projections, the rod having a first end, second end, and a middle portion between said first end and said second end; the first end having a hook for hooking around a second part of the skeleton, the middle portion having a flat part coterminous with said hook, and the second end having a threaded portion carrying a nut and being coterminous with said flat part;
   said leadway including a first bore and a second bore coaxial with said first bore, said second bore having a smaller diameter than the first bore so as to form an annular shoulder in the leadway where the first and second bores meet, said rod engaging a surface of said annular shoulder, and said nut having a recess for accommodating a tool.

2. The clamp according to claim 1 wherein said rod is positioned closer to said second projection than to said first projection, the rod coacts with said second projection so as to aid in positioning the second projection.

3. The clamp according to claim 2 wherein said second projection is longer than said first projection, said second projection being flat and thin, and said first projection having rounded contours.

4. The clamp according to claim 1 wherein said leadway is inclined at an angle with respect to a central plane extending through said first block.

5. The clamp according to claim 1 wherein said second projection is longer than said first projection, said second projection being flat and thin, and said first projection having rounded contours.

6. The clamp according to claim 1 wherein said first block has a penetrating hole extending therethrough.

7. The clamp according to claim 6 further comprising:
   a shaft positioned in said penetrating hole;
   a second block rotatably connected to said shaft;
   a means for screwing connected to said second block;
   a third block connected to said screwing means so that said second block and said third block are movable toward and away from each other resulting from a rotation of said screwing means; and
   a fourth block connected to said third block, said fourth block being attachable to a third part of the skeleton.

8. The clamp according to claim 1 wherein said fork lies in a plane which defines an angle with a central plane of said first block.

9. A surgical clamp for use in spinal surgery comprising:
   a rectangular first block defining a leadway, said leadway being inclined at an angle with respect to a central plane extending through said first block;
   a first projection having rounded contours, a second projection longer than said first projection and having a flat and thin shape, said first and second projections having parallel longitudinal axes and being mutually spaced and extending from said first block so as to form a fork for straddling a first part of a vertebra in a skeleton; and
   a tensioning means positioned in said leadway substantially parallel to the longitudinal axes of said first and second projections for fixing the clamp in a certain position, said tensioning means having a hook at one end for hooking a part of the skeleton different from said first part.

10. The clamp according to claim 9 wherein said tensioning means includes a rod having a first end, a second end, and a middle portion between said first end and said second end; the first end defining said hook, the middle portion having a flat part coterminous with said hook, and the second end having a threaded portion carrying a nut and being coterminous with said flat part.

11. The clamp according to claim 9 wherein said tensioning means is positioned closer to said second projection than to said first projection, the tensioning means coacts with said second projection so as to aid in positioning the second projection.

12. A surgical clamp comprising:
- a rectangular first block defining a leadway, the leadway including a first bore, a second bore coaxial with said first bore, said second bore having a smaller diameter than the first bore so as to form an annular shoulder in the leadway where the first and second bores meet;
- first and second projections extending from said first block having parallel longitudinal axes and being mutually spaced, the second projection being longer than the first projection; and
- a rod situated in said leadway substantially parallel to the longitudinal axes of said first and second projections, the rod having a first end, second end, and a middle portion between said first end and said second end; the first end having a hook, the middle portion having a flat part coterminous with said hook, and the second end having a threaded portion carrying a nut and being coterminous with said flat part.

13. The clamp according to claim 12 wherein said rod is positioned closer to said second projection than to said first projection, the rod coacting with said second projection so as to aid in positioning the second projection.

14. The clamp according to claim 12 wherein said leadway is inclined at an angle with respect to a central plane extending through said first block.

15. The clamp according to claim 12 wherein,
said rod engages a surface of said annular shoulder; and
said nut has a recess for accommodating a tool.

16. The clamp according to claim 12 wherein said second projection is flat and thin, and said first projection has rounded contours.

17. The clamp according to claim 12 wherein said first block has a penetrating hole extending therethrough.

18. The clamp according to claim 17 further comprising:
- a shaft positioned in said penetrating hole;
- a second block rotatably connected to said shaft;
- a means for screwing connected to said second block;
- a third block connected to said screwing means so that said second block and said third block are movable toward and away from each other resulting from a rotation of said screwing means; and
- a fourth block connected to said third block.

* * * * *